US006774064B1

(12) United States Patent
Reinehr et al.

(10) Patent No.: US 6,774,064 B1
(45) Date of Patent: Aug. 10, 2004

(54) ELASTANE PACKAGE

(75) Inventors: Ulrich Reinehr, Dormagen (DE); Tilo Sehm, Düsseldorf (DE); Wolfgang Anderheggen, Dormagen (DE); Toni Herbertz, Dormagen (DE)

(73) Assignee: Bayer Faser GmbH, Dormagen (DE)

( * ) Notice: Subject to any disclaimer, the term of this patent is extended or adjusted under 35 U.S.C. 154(b) by 0 days.

(21) Appl. No.: 09/958,422

(22) PCT Filed: Apr. 6, 2000

(86) PCT No.: PCT/EO00/03060

§ 371 (c)(1),
(2), (4) Date: Jan. 11, 2002

(87) PCT Pub. No.: WO00/63472

PCT Pub. Date: Oct. 26, 2000

(30) Foreign Application Priority Data

Apr. 19, 1999 (DE) .......................................... 199 17 529

(51) Int. Cl.⁷ ................................................ B32B 1/00
(52) U.S. Cl. ..................... 442/181; 428/397; 242/118; 242/159
(58) Field of Search ..................... 442/181; 428/397; 242/118, 159

(56) References Cited

U.S. PATENT DOCUMENTS 6,492,021 B1 * 12/2002 Reinehr et al. ............. 428/364

FOREIGN PATENT DOCUMENTS

WO    WO 00/00681    1/2000    ............. D01F/6/70

OTHER PUBLICATIONS

Patent Abstracts of Japan, publication No. 10152264, publication date Jun. 09, 1998 of application #08311517, application dated Nov. 22, 1996 of Toyobo Co Ltd.

Patent Abstracts of Japan, publication No. 01072726, publication date Mar. 17, 1989 of application #62230542, application dated Sep. 14, 1987 of Matsushita Electric Works Ltd.

English–language counterpart to WO 00/00681 (Specification—U.S. Ser. No. 09/720,768, filed Dec. 29, 2000).

* cited by examiner

*Primary Examiner*—Elizabeth M. Cole
(74) *Attorney, Agent, or Firm*—Norris McLaughlin & Marcus PA

(57) ABSTRACT

An elastance spool is described which comprises a winding of elastane threads having a titre of greater than 160 dtex, particularly from 160 dtex to 1400 dtex, and a bobbin weight of elastane threads of at least 1.5 kg, in which the elastane threads have a ribbon-shaped fiber cross-section, wherein the ratio of the width of the elastane threads to the thickness of the elastane threads in cross-section is at least three to one. The elastane spool is used for the production of textile sheet products and for the production of disposable articles of hygiene.

16 Claims, No Drawings

ELASTANE PACKAGE

This invention relates to an elastane spool comprising a winding of elastane threads having a titre of greater than 160 dtex, particularly from 160 dtex to 1400 dtex, and a bobbin weight of elastane threads of at least 1.5 kg, characterised in that the elastane threads have a ribbon-shaped fiber cross-section, wherein the ratio of the width of the elastane threads to the thickness of the elastane threads in cross-section is at least three to one.

This elastane spool is used for the production of textile sheet products and for the production of disposable articles of hygiene.

Elastane threads in the sense of the present invention are mono- or multi-filamentary continuous fibres, of which at least 85% by weight consist of segmented polyurethanes or polyurethane-ureas. The fiber-forming polymers have a segmented structure, i.e. they consist of "crystalline" and "amorphous" blocks ("hard segments" and "soft segments"). On account of their crystallinity, the hard segments act as fixed points of the network and are thus definitive for the strength of mouldings or fibres produced from these polymers. In contrast, the soft segments, the glass transition temperature of which has to be below the temperature of use, are definitive for the elasticity of these elastanes.

Elastanes of this type are usually produced by the addition polymerisation of long chain dihydroxyl compounds (macrodiols) with diisocyanates and low molecular weight dihydroxyl- or diamino compounds as chain lengtheners. Polyurethane-ureas which are obtained by chain lengthening with diamines are used for high-grade elastane filaments (also known as Spandex), firstly because they exhibit a high hard segment melting point compared with diol-lengthened polyurethanes, due to their larger number of hydrogen bonds between the polymer chains, and secondly because they exhibit excellent mechanical and elastic properties. Elastane threads are usually produced by spinning solutions of these segmented polyurethane-ureas in highly polar solvents such as dimethylformamide and dimethylacetamide, by means of what is termed the dry spinning processes or the wet spinning processes, or alternatively are produced by spinning from the melt, with a spinning solvent being dispensed with. After spinning, and optionally after conditioning, elastane threads are usually wound to form bobbins.

As a rule, the bobbin weights for elastane threads range from 0.5 to 1.5 kg, depending on the titre and on the field of use. However, there are fields of use where an even greater bobbin length of elastane threads is desirable. This is always the case if the further processing procedure in which the elastane threads are used must not be interrupted too often, which would result in more frequent machine stoppages and thus in additional undesirable costs.

An example of one of the aforementioned areas of use is the production of articles of hygiene, e.g. disposable nappies, in which elastic fibres are incorporated in nappy liners which contain an absorbent material. Good adaptability of these nappies to the corresponding body shape is thereby achieved. In general, 2–3 elastic fibres are incorporated on each longitudinal side of nappy liners. Elastane threads are generally incorporated in nappy liners by adhesive bonding with hot melt adhesives termed "hotmelts". Hot melt adhesives of this type, which are suitable for the structural adhesive bonding of PE and PP liners and of other nonwoven liners, for example, generally consist of isoprene/styrene-based synthetic rubbers, which are treated with mineral oils and additives in order to improve their flowability.

In order to achieve good adhesive bonding of elastane threads to nappy liners, the elastane threads should usually be produced as free as possible from conditioning agents or with a low content of conditioning agents.

Two processes which describe the production of elastane threads have hitherto become known in the prior art. Japanese Patent JP 2,000,038 describes elastane spools with a bobbin weight of at least 1.5 kg, wherein the conditioning agent content of the elastane threads on the bobbin is less than 2% by weight. The elastanes described there comprise a titre range from 308 to 1232 dtex, corresponding to about 280 to 1120 den.

Japanese Patent JP 10,305,060 claims elastane spools weighing more than 0.8 kg which are produced via a fiber reserve on another bobbin. For this purpose, elastane threads with the same titre range from 308 to 1232 dtex and with a conditioning agent content of 0.01–1% by weight are wound on bobbin spools.

In practice, this type of elastane spool is very difficult to process further, particularly if the bobbin weight is high, because elastane threads have a tendency to adhere to each other strongly. Due to the high bobbin weights, the outer layers of fibres of course press more intensively on the inner layers of fibres, so that after production and storage the fibres only run off the bobbins in an inferior manner. What is termed the "shoe sole effect" is observed here. This means that entire layers of fiber adhere to the bobbins and can no longer be unwound unless the elastane threads have already been conditioned to a sufficient extent during their production.

On the other hand, as mentioned above, the conditioning agent content of elastane threads on larger bobbins must not be too high, in order to achieve good adhesive bonding of the fibres to nappy liners.

Surprisingly, it has now been found that this problem can be solved by forming elastane threads from fibres which have a quite definite cross-sectional shape, so that even if the conditioning agent content of the elastane fiber on the bobbin is possibly relatively high, e.g. greater than 1% by weight, or in particular if it is even greater than 2% by weight, it is possible to achieve good adhesive bonding to nappy liners.

The present invention relates to an elastane spool comprising a winding of elastane threads having a titre of greater than 160 dtex, particularly from 160 dtex to 1400 dtex, and a bobbin weight of elastane threads of at least 1.5 kg, characterised in that the elastane threads have a ribbon-shaped fiber cross-section, wherein the ratio of the width of the elastane threads to the thickness of the elastane threads in cross-section is at least three to one, particularly at least five to one, more preferably at least seven to one, most preferably at least ten to one.

The bobbin weight of the elastane spool preferably ranges from 1.5 to 10 kg, particularly from 1.8 to 9 kg, most preferably from 3 to 8 kg.

As mentioned above, starting from elastane threads of defined cross-sectional shape, and despite a significantly higher content of conditioning agent, elastane threads can be produced on bobbins with bobbin weights from 1.5 to 5 kg or more, and can subsequently still be perfectly adhesively bonded under customary production conditions during their incorporation in nappy liners. A further advantage of the invention results from the fact that even finer elastane threads, of 150 dtex for example, can still be perfectly adhesively bonded, despite their reduced cross-sectional areas, by spraying on an adhesive. This is because they do not exist in the usual, compact, round cross-sectional shape, but exist in the form of a ribbon with a greater ribbon width.

Recycled material obtained from elastanes, which still contains considerable proportions of the original conditioning agents, is also particularly suitable for producing the elastanes of the elastane spools.

An elastane spool is preferred in which the elastane fiber has a content of conditioning agent of more than 1% by weight, particularly more than 2% by weight, most preferably more than 2.2% by weight, which is contained distributed in the fiber volume and/or on the fiber surface.

More especially, the elastane threads are multifilamentary and in particular comprise more than 80, preferably more than 160, most preferably more than 400 elementary filaments.

An elastane spool is particularly preferred which comprises a winding of elastane threads in which the individual spinning titre (IST) of the elementary filaments of the elastane threads is less than 15 dtex, preferably less than 10 dtex.

The elastane threads preferably consist of polyurethanes or polyurea-urethanes based on polyesters and/or polyethers.

The elastane threads of the bobbin are produced in particular by the melt spinning process, by the dry spinning process or by the wet spinning process. They are most preferably produced by the wet spinning process.

The cross-sectional shape of elastane threads substantially depends on the production process used. Whereas the dry spinning of elastane threads for medium and coarse titres above about 160 dtex from spinnerets comprising a plurality of spinneret holes produces conglutinated multifilaments which generally have roundish to oval overall cross-sectional shapes as determined over the entire cross-section, the use of a wet spinning process to produce titres above medium titres results in ribbon-shaped cross-sections strung in multiple rows, as on a string of beads. On account of their wide cross-sectional shape, adhesives can therefore be applied particularly well to these fibres, and the latter can be adhesively bonded particularly well to nappy liners, despite a relatively high oil content of more than 2% by weight.

Conditioning agents in the sense of the invention should be understood to comprise all types of additives which can be added to the elastane threads to improve their processability and to improve the build-up of the bobbin, particularly slip additives, wetting agents, lubricants, fiber sealing agents, etc. Suitable general types of conditioning agents and the function thereof are cited in "Synthesefasem", edited by B. v. Falkai, Verlag Chemie, 1981, page 111 et seq. Conditioning agents which are particularly suitable include mineral oils or paraffins, polysiloxanes, particularly polydimethylsiloxane or ethoxylated polydimethylsiloxane, metal salts of higher fatty acids such as palmitic acid, stearic acid or oleic acid, particularly the lithium, magnesium, zinc, aluminium or calcium salts thereof. Other suitable conditioning agents include antistatic agents such as sulphosuccinates, particularly dialkyl sulphosuccinates. Conditioning agents can be used in any combinations and mixtures.

The conditioning agents can be added either to the elastanes or elastane solution before spinning, or can also be deposited on the fibres after spinning, e.g. by means of conditioning agent rollers or spraying installations.

The elastane threads can contain a multiplicity of various other additives for various purposes, such as antioxidants, heat-, light- and UV radiation stabilisers, pigments and matting agents, dyes, lubricants and internal lubricants. Examples of antioxidants and of heat-, light- and UV radiation stabilisers include stabilisers from the group comprising sterically hindered phenols, HALS stabilisers (hindered amine light stabilisers), triazines, benzophenones and the benzotriazoles. Examples of pigments and matting agents include titanium dioxide, zinc oxide and barium sulphate. Examples of dyes include acidic dispersion dyes, pigment dyes and optical brighteners.

As is mentioned in the German Patent Application with the Patent Application Number 19829164.7, which has not yet been published, in a wet spinning process for elastane threads the ribbon shape can be widened by up to about 40% by increasing the number of filaments whilst the final titre remains constant, if the individual spinning titre of the individual fibres is less than 15 dtex, and in particular when it is 10 dtex at most. Elastane threads for which the width of the elastane threads in cross-section is at least the 3–5 times the ribbon thickness are particularly suitable as a bobbin material for the production of disposable articles of hygiene for example.

The present invention further relates to the use of the elastane spools according to the invention for the production of textile sheet products, particularly knitted fabric, woven fabric or looped fabrics, and for the production of disposable articles of hygiene, particularly nappy articles, e.g. for the bands of disposable nappies.

The ribbon width in the Examples is given in microns ($\mu$m). 1 cm corresponds to 10,000 microns.

The individual spinning titre (IST) is calculated as follows:

$$IST = \frac{F \cdot K \cdot 0.94 \cdot 100(dtex)}{A \cdot Z}$$

where:

F is the feed rate of spinning solution (ccm/min), K is the concentration of the spinning solution (% by weight), A is the velocity of the fibres in the regenerating bath (m/min) and Z is the number of spinneret holes.

The individual spinning titre is a measured quantity which gives the fiber weight immediately after the spinning solution emerges into the regeneration bath.

Measurement of the Conditioning Oil Content
Moisture determination R (%):

About 3 g elastane fiber were weighed out; weight=W1. The fibres were dried for 1 hour at 105° C. in a drying oven, allowed to cool to room temperature, and were subsequently re-weighed; weight=W2

$$\text{The moisture content } R\ (\%) = \frac{(W1 - W2) \times 100}{W2}$$

Determination of the Conditioning Agent Content D (%):

The fiber sample was introduced into a glass beaker and moistened with 100 ml of fresh petroleum ether. It was then vigorously stirred for 10 minutes at room temperature by a stirrer (magnetic stirrer). The sample was then removed from the beaker and was again vigorously stirred for 10 minutes with 100 ml of fresh petroleum ether. The petroleum ether was poured off and the fibres were dried in air. The fibres were subsequently treated for 5 minutes in 100 ml of boiling water and were dried for 1 hour at 105° C. in a drying oven, were allowed to cool to room temperature and were re-weighed; weight=W4.

The conditioning agent content D was then calculated as follows:

$$\left[\frac{1-\frac{W4}{W2}}{1+\frac{R}{100}}\right] \cdot 100$$

The following examples serve to provide a more detailed explanation of the invention.

Parts and percentages are given with respect to weight, unless indicated otherwise.

EXAMPLES

Example 1

A 30% by weight elastane spinning solution, which was produced according to Example 2 of DE-054222772, which had been pretreated with 0.5% diethylamine for about 12 minutes at 130° C., and which had a spinning viscosity of 23 Pa·s as measured at 50° C., was spun from four 172-hole spinnerets with a bore size of 0.1 mm into a regeneration bath comprising a 15% solution of DMAC in water. The fibres were drawn off at 60 m/min via a deflection roll which was situated just above the regeneration bath liquid, and were coalesced, washed, fixed at a velocity of 125 m/min over a heating roll, and conditioned, and the twisted fibres were wound up on a reeling machine. The fibres were taken up on spools of width 115 mm. 8 bobbins with a bobbin weight of 5 kg were produced. 106.5 ccm /min spinning solution were delivered from the spinning pump which supplied the four spinnerets. The individual spinning titre (IST) was 7.3 dtex. The elastane fiber, which had a final titre of 603 dtex, existed in the form of a closed ribbon. The ribbon width was about 1180 microns and the ribbon thickness was about 190 microns. The ratio of ribbon width to ribbon thickness was thus 6.2 to 1. The elastane threads had a moisture content R of 0.17% and a conditioning agent content of 2.23%. 8 elastane spools with a bobbin weight of 5 kg were placed on a take-off stand on a production line for disposable nappies and were adhesively bonded to pre-placed nappy liners, at 160 m/min and under production conditions, by spraying on hot melt adhesive (hotmelt; Lunatack D3937, manufactured by H. B. Fuller GmbH). The finished nappies exhibited very good bonding between the incorporated elastane threads and the nappy liners (bond examinations in blue light).

Example 2

Part of the spinning solution from Example 1 was spun from four 96-hole spinnerets with a bore size of 0.1 mm into a regeneration bath comprising a 15% solution of DMAC in water. The fibres were drawn off at 90 m/min, and were coalesced, washed, fixed at a velocity of 150 m/min over a heating roll, and conditioned, and the twisted fibres were wound up on a reeling machine. The fibres were taken up on spools of spool width 115 mm. 8 bobbins with a bobbin weight of 1.5 kg were produced. 31.6 ccm/min spinning solution were delivered from the spinning pump which supplied the four spinnerets. The individual spinning titre (IST) was 2.6 dtex. The elastane fiber, which had a final titre of 149 dtex, again existed in the form of a closed ribbon. The ribbon width was about 450 microns and the ribbon thickness was about 65 microns. The ratio of ribbon width to ribbon thickness was 7 to 1. The elastane threads had a moisture content R of 0.14% and a conditioning agent content of 2.11%. 8 elastane spools with a bobbin weight of 1.5 kg were placed on a rewinding stand on a production line for disposable nappies and were processed with nappy liners, as described in Example 1, to form finished nappies. The finished nappies again exhibited good bonding between the incorporated elastane threads and the nappy liners.

Example 3

A 30% by weight elastane spinning solution, which was prepared as in Example 1, was produced from recycled material according to Example 1 of Application FAS 13, blended in a ratio of 1:1, and was converted as described there into a spinning solution with a spinning viscosity of 18 Pa·s. as measured at 50° C. The spinning solution was spun from four 172-hole spinnerets with a bore size of 0.15 mm into a regeneration bath comprising a 20% solution of DMAC in water. The fibres were subsequently drawn off at 70 m/min, and were coalesced, washed, fixed at a velocity of 130 m/min over a heating roll, and conditioned, and the twisted fibres were again wound up on a reeling machine. The fibres were taken up on spools of width 115 mm. 8 bobbins with a bobbin weight of 3 kg were produced. 110.8 ccm/min spinning solution were delivered from the spinning pump which supplied the 4 spinnerets. The individual spinning titre (IST) was 6.5 dtex. The elastane fiber, which had a final titre of 598 dtex, again existed in the form of a closed ribbon. The ribbon width was about 1100 microns and the ribbon thickness was 200 microns. The ratio of ribbon width to ribbon thickness was thus 5.5 to 1. The elastane threads had a moisture content R of 0.17% and a conditioning agent content D of 4.29%. 8 elastane spools with a bobbin weight of 3 kg were placed on a production line for disposable nappies as described in Example 1 and were incorporated in nappy liners. The finished nappies exhibited very good bonding between the incorporated elastane threads and the nappy liners.

Example 4

Part of the spinning solution from Example 3 was spun from four 96-hole spinnerets with a bore size of 0.2 mm, as described in Example 3, into a regeneration bath comprising a 10% solution of DMAC in water. The fibres were subsequently drawn off at 80 m/min, and were coalesced, washed, fixed at a velocity of 125 m/min over a heating roll, conditioned, and wound up on a reeling machine. 8 bobbins with a bobbin weight of 3 kg were again produced. 142.7 ccm/nin spinning solution were delivered from the spinning pump which supplied the 4 spinnerets. The individual spinning titre (IST) was 13.1 dtex. The elastane fiber, which had a final titre of 805 dtex, again existed in the form of a closed ribbon. The ribbon width was about 760 microns and the ribbon thickness was about 250 microns. The ratio of ribbon width to ribbon thickness was thus about 3 to 1. The elastane threads had a moisture content R of 0.2% and a conditioning agent content D of 3.88%, distributed over the entire fiber cross-section. 8 elastane spools with a bobbin weight of 3 kg were again placed on a production line for disposable nappies as described in Example 1 and were incorporated in nappy liners. As shown by bond examinations performed on nappies under irradiation with blue light, there was again very good bonding between the elastane threads and the nappy liners.

Example 5

A 30% by weight spinning solution, which was produced from pure recycled material according to Example 2 of Application FAS 13, with a spinning viscosity of 22 Pa·s. as measured at 50° C., was spun from two 441-hole spinnerets with a bore size of 0.12 mm into a regeneration bath comprising a 18% solution of DMAC in water. The fibres were drawn off at 60 m/min, and were coalesced, washed, fixed at a velocity of 130 m/min over a heating roll, conditioned, and wound up on a reeling machine. 8 bobbins with a bobbin weight of 2.4 kg were produced. 129 ccm/min spinning solution were delivered from the spinning pump which supplied the two spinnerets.

The individual spinning titre (IST) was 6.9 dtex. The elastane fiber, which had a final titre of 1402 dtex, again existed in the form of a closed ribbon. The ribbon width was 3330 microns and the ribbon thickness was about 320 microns. The ratio of ribbon width to ribbon thickness was thus 10.4 to 1. The elastane threads had a moisture content R of 0.2% and a conditioning agent content D of 2.67%, distributed over the entire fiber cross-section. 8 elastane spools with a bobbin weight of 2.4 kg were again placed on a production line for disposable nappies and were incorporated in nappy liners. As shown by bond examinations performed on nappies under irradiation with blue light, there was again very good bonding between the elastane threads and the nappy liners.

What is claimed is:

1. An elastane spool comprising a winding of elastane threads having a titre of greater than 160 dtex and a bobbin weight of elastane threads of 1.8 to 9 kg, wherein the elastane threads have a ribbon-shaped fiber cross-section, the ratio of the width of the elastane threads to the thickness of the elastane threads in cross-section being at least three to one.

2. An elastane spool according to claim 1, wherein the bobbin weight ranges from 3 to 8 kg.

3. An elastane spool according to claim 1, wherein the elastane fibre has a content of conditioning agent of more than 1% by weight, which is distributed within the fibre volume, on the fibre surface or both.

4. An elastane spool according to claim 1, wherein the elastane threads are multi-filamentary and comprise more than 80 elementary filaments.

5. An elastane spool according to claim 1, wherein the individual spinning titre (IST) of the elementary filaments of the elastane threads is less than 15 dtex.

6. An elastane spool according to claim 1, wherein the elastane threads consist of polyurethanes or polyurea-urethanes based on polyesters, polyethers.

7. An elastane spool according to claim 1, wherein the elastane threads are produced by the melt spinning process, the dry spinning process or the wet spinning process.

8. The elastane spool of claim 1, wherein said ratio is at least five to one.

9. The elastane spool of claim 1, wherein said ratio is at least seven to one.

10. The elastane spool of claim 9, wherein said ratio is at least ten to one.

11. The elastane spool of claim 3, wherein said content of conditioning agents is more than 2.2% by weight.

12. The elastane spool of claim 11, wherein said content of conditioning agent is more than 2.2% by weight.

13. The elastane spool of claim 4, wherein said threads comprise more than 160 elementary filaments.

14. The elastane spool of claim 1, wherein said threads comprise more than 400 elementary filaments.

15. The elastane spool of claim 5, wherein said individual spinning titre is less than 10 dtex.

16. The elastane spool of claim 7, wherein said threads are produced by the wet spinning process.

* * * * *

UNITED STATES PATENT AND TRADEMARK OFFICE
CERTIFICATE OF CORRECTION

PATENT NO.     : 6,774,064 B1
DATED          : August 10, 2004
INVENTOR(S)    : Reinehr et al.

It is certified that error appears in the above-identified patent and that said Letters Patent is hereby corrected as shown below:

<u>Title page,</u>
Item [57], ABSTRACT,
Line 5, "fiber" should read -- fibre --

<u>Column 1,</u>
Line 7, "fiber" should read -- fibre --
Line 17, "fiber-forming" should read -- fibre-forming --

<u>Column 2,</u>
Lines 13, 26 and 37, "fiber" should read -- fibre --
Line 39, "weight," should read -- weight, --
Line 47, "fiber"should read -- fibre --

<u>Column 3,</u>
Line 5, "fiber" should read -- fibre --
Line 9, "fiber volume and/or on the fiber surface" should read -- fibre volume and/or on the fibre surface --
Line 43, "fiber sealing" should read -- fibre sealing --

<u>Column 4,</u>
Line 38, "fiber weight" should read -- fibre weight --
Lines 43 and 55, "fiber" should read -- fibre --
Line 38, "fiber weight" should read -- fibre weight --
Lines 43 and 55, "fiber" should read -- fibre --

<u>Column 5,</u>
Lines 32 and 60, "elastane fiber" should read -- elastane fibre --
Line 23, "elastane fiber" should read -- elastane fibre --
Line 46, "ccm/nin" should read -- ccm/min --
Line 48, "ccm/nin" should read -- ccm/min --

UNITED STATES PATENT AND TRADEMARK OFFICE
CERTIFICATE OF CORRECTION

PATENT NO. : 6,774,064 B1
DATED : August 10, 2004
INVENTOR(S) : Reinehr et al.

It is certified that error appears in the above-identified patent and that said Letters Patent is hereby corrected as shown below:

<u>Column 7,</u>
Line 10, "elastane fiber" should read -- elastane fibre --
Lines 16 and 27, "fiber cross-section" should read -- fibre cross-section --

Signed and Sealed this

Thirty-first Day of May, 2005

JON W. DUDAS
*Director of the United States Patent and Trademark Office*